United States Patent
Renee

(10) Patent No.: US 12,011,340 B2
(45) Date of Patent: Jun. 18, 2024

(54) HEARING PROTECTION ASSEMBLY

(71) Applicant: Andrew Renee, Rosedale, NY (US)

(72) Inventor: Andrew Renee, Rosedale, NY (US)

(*) Notice: Subject to any disclaimer, the term of this patent is extended or adjusted under 35 U.S.C. 154(b) by 496 days.

(21) Appl. No.: 17/317,553

(22) Filed: May 11, 2021

(65) Prior Publication Data

US 2022/0362058 A1 Nov. 17, 2022

(51) Int. Cl.
*A61F 11/14* (2006.01)
*A41D 13/11* (2006.01)

(52) U.S. Cl.
CPC .......... *A61F 11/14* (2013.01); *A41D 13/1161* (2013.01)

(58) Field of Classification Search
CPC ............... A41D 13/1161; A41D 20/00; A61M 16/0605; A45D 44/00; A45D 44/12; A61F 11/06; A61F 11/14; A61F 9/029; A61F 11/12; A61F 9/027; A61F 11/08; A61F 2007/0005; A61F 2250/0023; A61F 7/007; A63B 71/10
See application file for complete search history.

(56) References Cited

U.S. PATENT DOCUMENTS

| | | | |
|---|---|---|---|
| 3,541,611 A * | 11/1970 | Beguin | A42B 3/166 2/209 |
| 5,179,736 A | 1/1993 | Scanlon | |
| 6,481,846 B1 | 11/2002 | Mikysa | |
| 8,621,664 B2 | 1/2014 | Peebles | |
| D776,082 S | 1/2017 | Williams | |
| 10,076,149 B2 | 9/2018 | Ross | |
| 2009/0145444 A1 | 6/2009 | Edwards | |
| 2019/0008228 A1 | 1/2019 | Ramey | |

FOREIGN PATENT DOCUMENTS

CN 209864275 U * 12/2019
WO WO2013159221 10/2013

* cited by examiner

*Primary Examiner* — Ophelia A Hawthorne

(57) ABSTRACT

A hearing protection assembly for wearing a face mask with ear muffs includes a pair of ear muffs that can be worn over a user's ears thereby facilitating the ear muffs to protect the user from being exposed to excessive sound levels. Each of the ear muffs has a groove integrated therein to accommodate a respective one of a pair of ear loops of a face mask when the ear muffs and the face mask are both worn. A plurality of straps is each coupled to a respective one of the ear muffs. Each of the straps is extendable across the groove in the respective ear muff to retain the respective ear loop of the face mask in the groove in the respective ear muff.

6 Claims, 3 Drawing Sheets

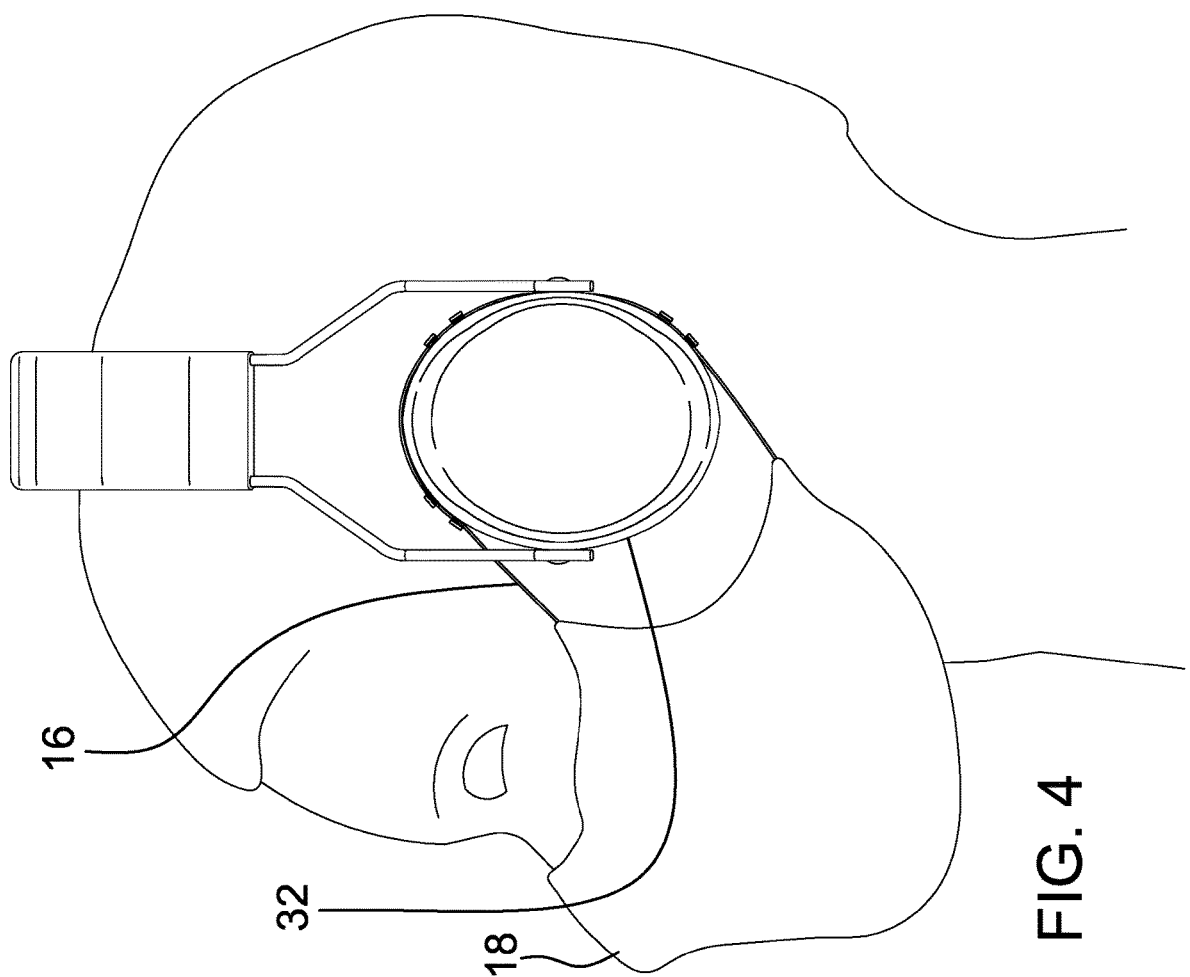
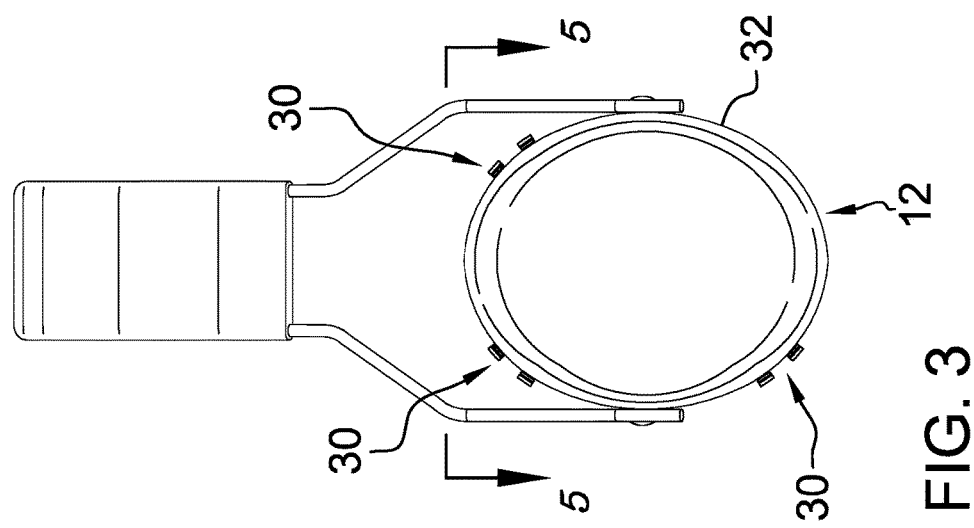

HEARING PROTECTION ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to protection devices and more particularly pertains to a new protection device for wearing a face mask with ear muffs. The device includes grooves recessed into ear muffs that can accommodate ear loops of a face mask. Additionally, a plurality of straps is extendable over the grooves to retain the ear loops in the respective groove.

(2) Description of Related Art Including Information Disclosed Under 37 CFR 1.97 and 1.98

The prior art relates to protection devices including a pair of ear muffs that has a face shield being pivotally coupled thereto. Additionally, the prior art discloses a variety of ear muffs which have various means of eye protection being coupled thereto. In no instance does the prior art disclose ear muffs with a groove integrated therein, for receiving an ear loop of a face mask, and a plurality of straps that are extendable across the groove.

BRIEF SUMMARY OF THE INVENTION

An embodiment of the disclosure meets the needs presented above by generally comprising a pair of ear muffs that can be worn over a user's ears thereby facilitating the ear muffs to protect the user from being exposed to excessive sound levels. Each of the ear muffs has a groove integrated therein to accommodate a respective one of a pair of ear loops of a face mask when the ear muffs and the face mask are both worn. A plurality of straps is each coupled to a respective one of the ear muffs. Each of the straps is extendable across the groove in the respective ear muff to retain the respective ear loop of the face mask in the groove in the respective ear muff.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 3 is a right side view of an embodiment of the disclosure.

FIG. 4 is a perspective in-use view of an embodiment of the disclosure.

DETAILED DESCRIPTION OF THE INVENTION

Figure 1:
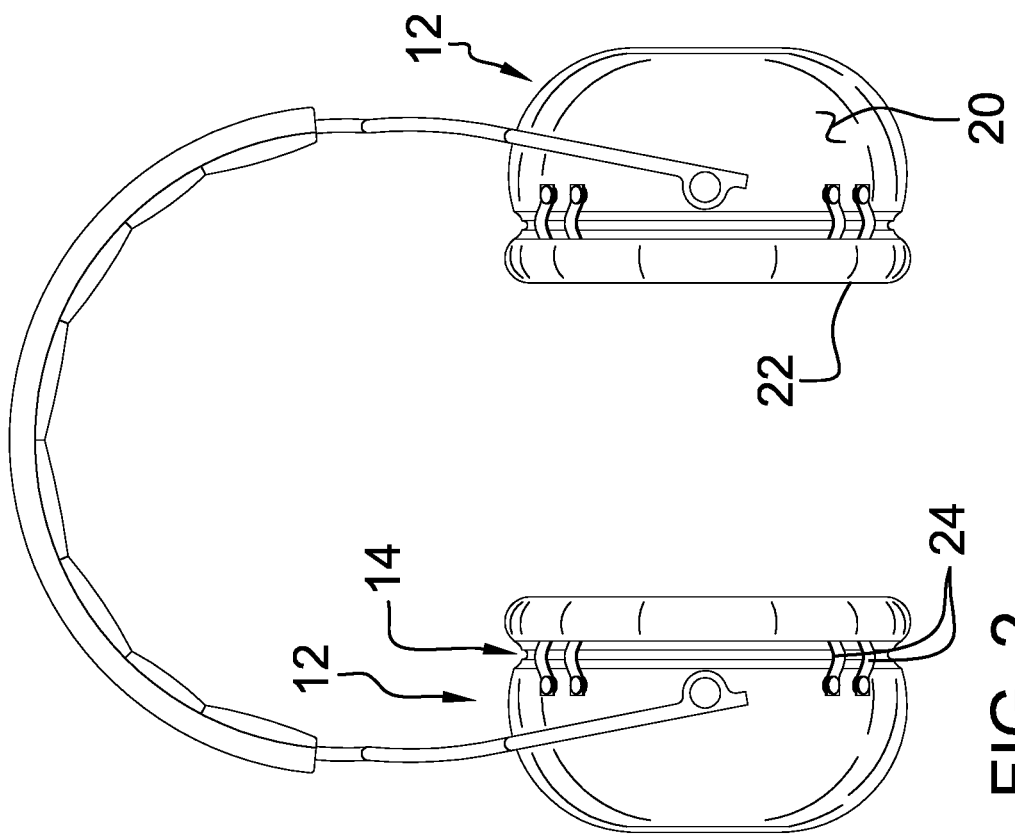
FIG. 1 is a front view of a hearing protection assembly according to an embodiment of the disclosure.
Figure 2:
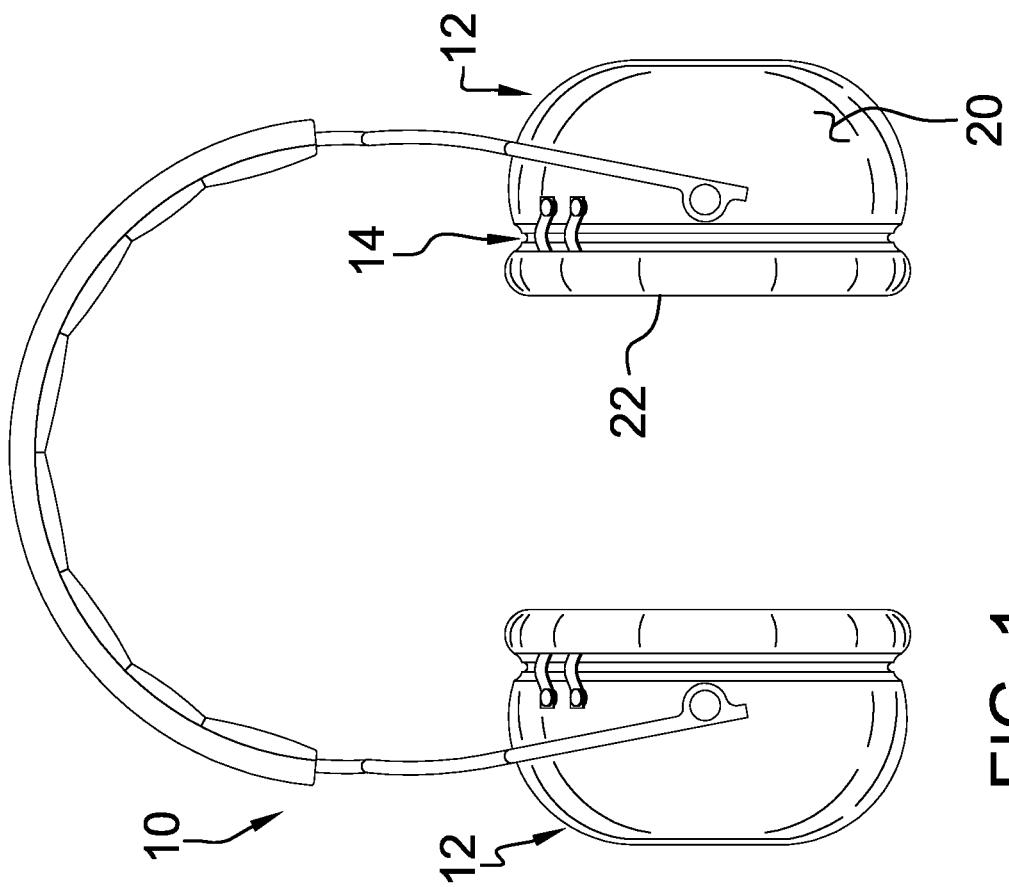
FIG. 2 is a back view of an embodiment of the disclosure.
Figure 5:
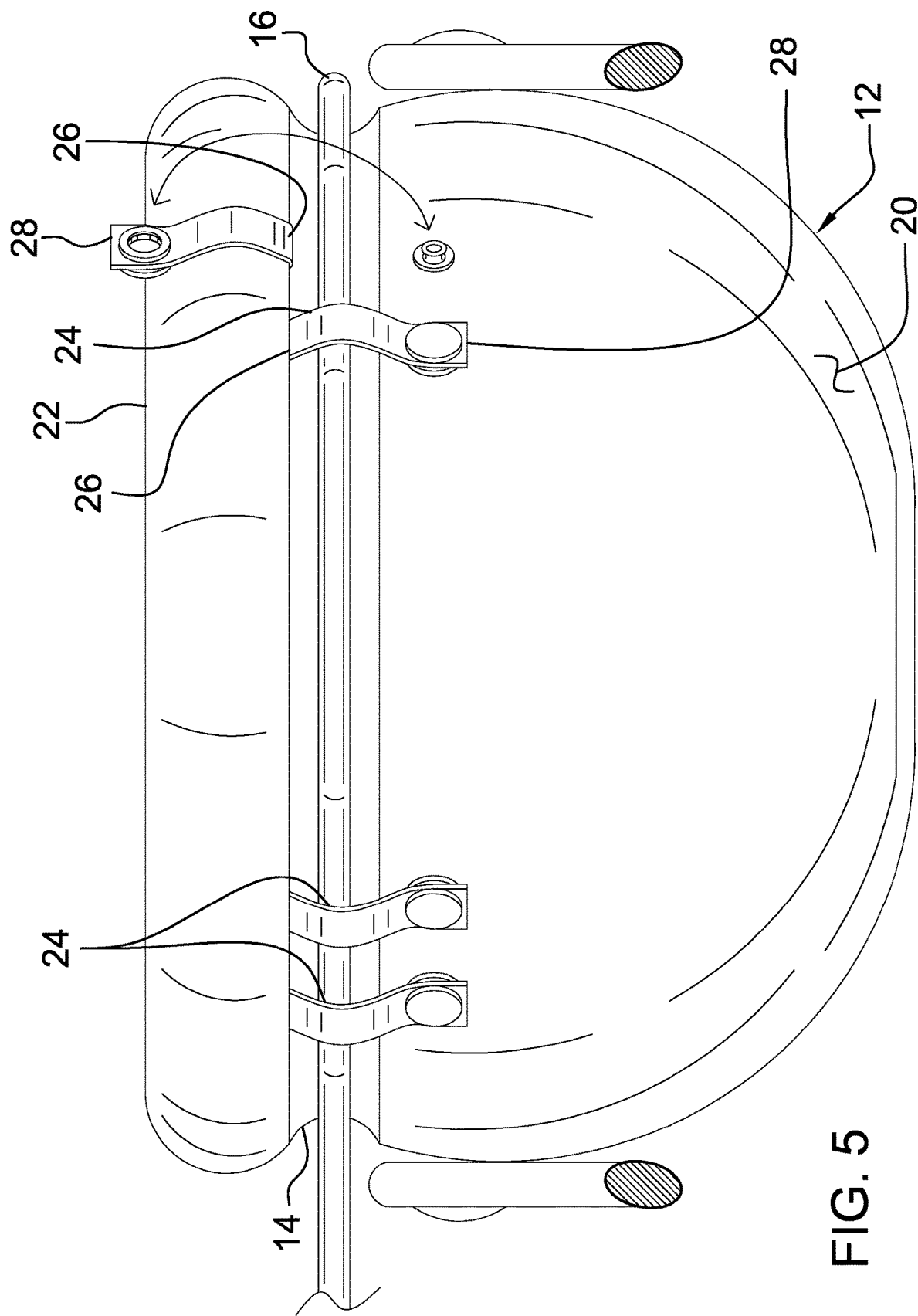
FIG. 5 is a cross sectional view taken along line 5-5 of FIG. 3 of an embodiment of the disclosure.

With reference now to the drawings, and in particular to FIGS. 1 through 5 thereof, a new protection device embodying the principles and concepts of an embodiment of the disclosure and generally designated by the reference numeral 10 will be described.

As best illustrated in FIGS. 1 through 5, the hearing protection assembly 10 generally comprises a pair of ear muffs 12 that can be worn over a user's ears thereby facilitating the ear muffs 12 to protect the user from being exposed to excessive sound levels. The ear muffs 12 may be ear muffs that meet NIOSH guidelines for personal protective equipment related to hearing protection. In this way the ear muffs 12 can be worn on construction sites, for example, or any other environment where the user would be exposed to sound levels in excess of 85.0 dBA.

Each of the ear muffs 12 has a groove 14 integrated therein and the groove 14 in each of the ear muffs 12 can accommodate a respective one of a pair of ear loops 16 of a face mask 18 when the ear muffs 12 and the face mask 18 are both worn. The face mask 18 may be an N95 filter or other type of face mask that is approved for use during the Covid pandemic. Each of the ear muffs 12 has an outer surface 20 and an inwardly facing side 22, and the inwardly facing side 22 of each of the ear muffs 12 is directed toward each other to accommodate a respective one of the user's ears. The groove 14 in each of the ear muffs 12 is recessed into the outer surface 20, and the groove 14 in each of the ear muffs 12 extends around a full diameter of the respective ear muff 12. Additionally, the groove 14 in each of the ear muffs 12 is positioned adjacent to the inwardly facing side 22.

A plurality of straps 24 is each coupled to a respective one of the ear muffs 12. Each of the straps 24 is extendable across the groove 14 in the respective ear muff 12 to retain the respective ear loop 16 of the face mask 18 in the groove 14 in the respective ear muff 12. Each of the straps 24 is releasably matable to the respective ear muff 12 when the straps 24 are extended across the groove 14 in each of the ear muffs 12. Each of the straps 24 has a first end 26 and a second end 28, and the first end 26 of each of the straps 24 is coupled to the outer surface 20 of the respective ear muff 12. Additionally, the first end 26 of each of the straps 24 is positioned between the groove 14 and the inwardly facing side 22 of the respective ear muff 12. The plurality of straps 24 is arranged into a plurality of sets of the straps 30. Each of the sets of straps 30 is spaced apart from each other and is distributed around the outer surface 20 of the respective ear muff 12. As is most clearly shown in FIG. 4, the sets of straps 30 are not present on a front side 32 of each of the ear muffs 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A hearing protection assembly for wearing over a user's ears and which can accommodate ear loops of a face mask being worn by the user, said assembly comprising:
   a pair of ear muffs being configured to be worn over a user's ears thereby facilitating said ear muffs to protect the user from being exposed to excessive sound levels, each of said ear muffs having a groove being integrated therein wherein said groove in each of said muffs is configured to accommodate a respective one of a pair of ear loops of a face mask when said ear muffs and the face mask are both worn;
   a plurality of straps, each of said straps being coupled to a respective one of said ear muffs, each of said straps being extendable across said groove in said respective ear muff wherein each of said straps is configured to retain the respective ear loop of the face mask in said groove in said respective ear muff, each of said straps being releasably matable to said respective ear muff when said straps are extended across said groove in each of said ear muffs;
   wherein each of said ear muffs has an outer surface and an inwardly facing side, said inwardly facing side of each of said ear muffs being directed toward each other wherein said inwardly facing side of each of said ear muffs is configured to accommodate a respective one of the user's ears, said groove in each of said ear muffs being recessed into said outer surface, said groove in each of said ear muffs extending around a full diameter of said respective ear muff, said groove in each of said ear muffs being positioned adjacent to said inwardly facing side; and
   wherein each of said straps has a first end and a second end, said first end of each of said straps being coupled to said outer surface of said respective ear muff, said first end of each of said straps being positioned between said groove and said inwardly facing side of said respective ear muff, said plurality of straps being arranged into a plurality of sets of said straps, each of said sets of straps being spaced apart from each other and being distributed around said outer surface of said respective ear muff.

2. The assembly according to claim 1, further comprising a plurality of first fasteners, each of said first fasteners being coupled to a respective one of said straps, each of said first fasteners being aligned with said second end of said respective strap.

3. The assembly according claim 2, further comprising a plurality of second fasteners, each of said second fasteners being coupled to said outer surface of a respective one of said ear muffs, each of said second fasteners being positioned on an opposite side of said groove with respect to said first end of said straps, each of said second fasteners being aligned with a respective one of said straps, said first fastener on each of said straps releasably engaging a respective one of said second fasteners for retaining said straps in an orientation extending across said groove in said receptive ear muff.

4. A hearing protection assembly for wearing over a user's ears and which can accommodate ear loops of a face mask being worn by the user, said assembly comprising:
   a pair of ear muffs being configured to be worn over a user's ears thereby facilitating said ear muffs to protect the user from being exposed to excessive sound levels, each of said ear muffs having a groove being integrated therein wherein said groove in each of said ear muffs is configured to accommodate a respective one of a pair of ear loops of a face mask when said ear muffs and the face mask are both worn;
   a plurality of straps, each of said straps being coupled to a respective one of said ear muffs, each of said straps being extendable across said groove in said respective ear muff wherein each of said straps is configured to retain the respective ear loop of the face mask in said groove in said respective ear muff, each of said straps being releasably ratable to said respective ear muff when said straps are extended across said groove in each of said ear muffs; and
   wherein each of said ear muffs has an outer surface and an inwardly facing side, said inwardly facing side of each of said ear muffs being directed toward each other wherein said inwardly facing side of each of said ear muffs is configured to accommodate a respective one of the user's ears, said groove in each of said ear muffs being recessed into said outer surface, said groove in each of said ear muffs extending around a full diameter of said respective ear muff, said groove in each of said ear muffs being positioned adjacent to said inwardly facing side.

5. The assembly according to claim 4, further comprising:
   each of said straps having a first end and a second end, said first end of each of said straps being coupled to said outer surface of said respective ear muff, said first end of each of said straps being positioned between said groove and said inwardly facing side of said respective ear muff, said plurality of straps being arranged into a plurality of sets of said straps, each of said sets of straps being spaced apart from each other and being distributed around said outer surface of said respective ear muff;

a plurality of first fasteners, each of said first fasteners being coupled to a respective one of said straps, each of said first fasteners being aligned with said second end of said respective strap; and a plurality of second fasteners, each of said second fasteners being coupled to said outer surface of a respective one of said ear muffs, each of said second fasteners being positioned on an opposite side of said groove with respect to said first end of said straps, each of said second fasteners being aligned with a respective one of said straps, said first fastener on each of said straps releasably engaging a respective one of said second fasteners for retaining said straps in an orientation extending across said groove in said receptive ear muff.

6. A hearing protection system for wearing over a user's ears and which can accommodate ear loops of a face mask being worn by the user, said assembly comprising:

a face mask having a pair of ear loops wherein said face mask is configured to be worn on a user's face;

a pair of ear muffs being configured to be worn over a user's ears thereby facilitating said ear muffs to protect the user from being exposed to excessive sound levels, each of said ear muffs having a groove being integrated therein, said groove in each of said ear muffs accommodating a respective one of said ear loops of said face mask when said ear muffs and said face mask are both worn, each of said ear muffs having an outer surface and an inwardly facing side, said inwardly facing side of each of said ear muffs being directed toward each other wherein said inwardly facing side of each of said ear muffs is configured to accommodate a respective one of the user's ears, said groove in each of said ear muffs being recessed into said outer surface, said groove in each of said ear muffs extending around a full diameter of said respective ear muff, said groove in each of said ear muffs being positioned adjacent to said inwardly facing side;

a plurality of straps, each of said straps being coupled to a respective one of said ear muffs, each of said straps being extendable across said groove in said respective ear muff to retain said respective ear loop of said face mask in said groove in said respective ear muff, each of said straps being releasably matable to said respective ear muff when said straps are extended across said groove in each of said ear muffs, each of said straps having a first end and a second end, said first end of each of said straps being coupled to said outer surface of said respective ear muff, said first end of each of said straps being positioned between said groove and said inwardly facing side of said respective ear muff, said plurality of straps being arranged into a plurality of sets of said straps, each of said sets of straps being spaced apart from each other and being distributed around said outer surface of said respective ear muff;

a plurality of first fasteners, each of said first fasteners being coupled to a respective one of said straps, each of said first fasteners being aligned with said second end of said respective strap; and a plurality of second fasteners, each of said second fasteners being coupled to said outer surface of a respective one of said ear muffs, each of said second fasteners being positioned on an opposite side of said groove with respect to said first, end of said straps, each of said second fasteners being aligned with a respective one of said straps, said first fastener on each of said straps releasably engaging a respective one of said second fasteners for retaining said straps in an orientation extending across said groove in said receptive ear muff.

\* \* \* \* \*